United States Patent
Blau et al.

(10) Patent No.: US 10,588,647 B2
(45) Date of Patent: Mar. 17, 2020

(54) COMPUTER ASSISTED SURGERY SYSTEM

(75) Inventors: Arno Blau, Basel (CH); Bernd Simon, Kiel (DE); Holger Müller-Daniels, Gettorf (DE); Michael Kohnen, Heitersheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 656 days.

(21) Appl. No.: 12/715,113

(22) Filed: Mar. 1, 2010

(65) Prior Publication Data

US 2011/0213379 A1    Sep. 1, 2011

(51) Int. Cl.
| | | |
|---|---|---|
| *A61B 17/17* | (2006.01) | |
| *A61B 34/10* | (2016.01) | |
| *A61B 17/72* | (2006.01) | |
| *G06F 19/00* | (2018.01) | |
| *A61B 90/00* | (2016.01) | |
| *G16H 50/50* | (2018.01) | |

(52) U.S. Cl.
CPC ...... *A61B 17/1703* (2013.01); *A61B 17/1717* (2013.01); *A61B 34/10* (2016.02); *A61B 17/1721* (2013.01); *A61B 17/72* (2013.01); *A61B 2034/102* (2016.02); *A61B 2090/376* (2016.02); *G06F 19/3481* (2013.01); *G16H 50/50* (2018.01)

(58) Field of Classification Search
CPC ... A61B 17/1753; A61B 17/173; A61B 19/50; A61B 2019/502; A61B 90/39; A61B 2090/3975
USPC .......................... 600/424, 410, 416; 606/102
See application file for complete search history.

(56) References Cited

U.S. PATENT DOCUMENTS

| | | |
|---|---|---|
| 4,475,545 A | 10/1984 | Ender |
| 4,622,959 A | 11/1986 | Marcus |
| 5,122,141 A | 6/1992 | Simpson et al. |
| 5,436,542 A | 7/1995 | Petelin et al. |
| 5,480,402 A | 1/1996 | Kim |
| 5,533,143 A | 7/1996 | Takeo |
| 5,622,170 A | 4/1997 | Schulz |

(Continued)

FOREIGN PATENT DOCUMENTS

| | | |
|---|---|---|
| CN | 1424673 A | 6/2003 |
| CN | 1203435 C | 5/2005 |

(Continued)

OTHER PUBLICATIONS

Baumgaertner et al. "The Value of the Tip-Apex Distance in Predicting Failure of Fixation of Peritrochanteric Fractures of the Hip. The Journal of Bone & Joint Surgery". 1995;77:1058-1064 (Year: 1995).*

(Continued)

*Primary Examiner* — Angela M Hoffa
*Assistant Examiner* — Helene Bor
(74) *Attorney, Agent, or Firm* — Lerner, David, Littenberg, Krumholz & Mentlik, LLP

(57) ABSTRACT

A computer assisted surgery system and a method for operating a computer assisted surgery system is described therein. The system and method includes providing a virtual representation of a medical device to provide an easier application of a medical device, such as an implant or the like. The described system and method allows for simple and fast positioning of a medical device to be applied, such as an implant, for example.

15 Claims, 10 Drawing Sheets

(56) References Cited

U.S. PATENT DOCUMENTS

| | | | |
|---|---|---|---|
| 5,682,886 A | 11/1997 | Delp et al. | |
| 5,799,055 A | 8/1998 | Peshkin et al. | |
| 5,841,830 A | 11/1998 | Barni et al. | |
| 5,880,976 A | 3/1999 | DiGioia, III et al. | |
| 6,002,859 A | 12/1999 | DiGioia, III et al. | |
| 6,021,343 A | 2/2000 | Foley et al. | |
| 6,053,918 A | 4/2000 | Spievack | |
| 6,069,932 A | 5/2000 | Peshkin et al. | |
| 6,074,394 A * | 6/2000 | Krause | A61B 17/1707 606/86 R |
| 6,101,543 A | 8/2000 | Alden et al. | |
| 6,149,592 A | 11/2000 | Yanof et al. | |
| 6,198,794 B1 | 3/2001 | Peshkin et al. | |
| 6,205,411 B1 | 3/2001 | DiGioia, III et al. | |
| 6,221,074 B1 | 4/2001 | Cole et al. | |
| 6,226,548 B1 | 5/2001 | Foley et al. | |
| 6,285,902 B1 | 9/2001 | Kienzle, III et al. | |
| 6,341,231 B1 | 1/2002 | Ferre et al. | |
| 6,370,421 B1 | 4/2002 | Williams et al. | |
| 6,428,547 B1 * | 8/2002 | Vilsmeier et al. | 606/130 |
| 6,450,978 B1 | 9/2002 | Brosseau et al. | |
| 6,470,207 B1 | 10/2002 | Simon et al. | |
| 6,477,400 B1 | 11/2002 | Barrick | |
| 6,503,249 B1 | 1/2003 | Krause | |
| 6,510,241 B1 | 1/2003 | Vaillant et al. | |
| 6,535,756 B1 | 3/2003 | Simon et al. | |
| 6,674,883 B1 | 1/2004 | Wei et al. | |
| 6,697,664 B2 | 2/2004 | Kienzle, III et al. | |
| 6,701,174 B1 | 3/2004 | Krause et al. | |
| 6,711,432 B1 | 3/2004 | Krause et al. | |
| 6,718,194 B2 | 4/2004 | Kienzle, III | |
| 6,725,080 B2 | 4/2004 | Melkent et al. | |
| 6,747,646 B2 | 6/2004 | Gueziec et al. | |
| 6,810,280 B2 | 10/2004 | Strobel | |
| 6,856,826 B2 | 2/2005 | Seeley et al. | |
| 6,887,245 B2 | 5/2005 | Kienzle, III et al. | |
| 6,917,827 B2 * | 7/2005 | Kienzle, III | 600/427 |
| 6,922,581 B2 | 7/2005 | Kienzle, III | |
| 7,130,676 B2 | 10/2006 | Barrick | |
| 7,167,738 B2 | 1/2007 | Schweikard et al. | |
| 7,203,277 B2 | 4/2007 | Birkenbach et al. | |
| 7,235,076 B2 | 6/2007 | Pacheco | |
| 7,247,157 B2 | 7/2007 | Prager et al. | |
| RE40,176 E | 3/2008 | Peshkin et al. | |
| 7,392,076 B2 | 6/2008 | Moctezuma de la Barrera | |
| 7,427,200 B2 | 9/2008 | Noble et al. | |
| 7,427,272 B2 | 9/2008 | Richard et al. | |
| 7,567,834 B2 | 7/2009 | Clayton et al. | |
| 7,570,791 B2 | 8/2009 | Frank et al. | |
| 7,726,002 B2 | 6/2010 | Shimp et al. | |
| 7,887,545 B2 | 2/2011 | Fernandez et al. | |
| 7,914,532 B2 | 3/2011 | Shaver et al. | |
| 7,966,058 B2 | 6/2011 | Xue et al. | |
| 8,090,166 B2 | 1/2012 | Rappaport et al. | |
| 8,611,697 B2 | 12/2013 | Nathaniel et al. | |
| 9,109,998 B2 | 8/2015 | Nathaniel et al. | |
| 9,111,180 B2 | 8/2015 | Rappaport et al. | |
| 9,433,390 B2 | 9/2016 | Nathaniel et al. | |
| 2001/0036245 A1 | 11/2001 | Kienzle et al. | |
| 2002/0188194 A1 | 12/2002 | Cosman | |
| 2004/0009459 A1 | 1/2004 | Anderson et al. | |
| 2004/0030245 A1 | 2/2004 | Noble et al. | |
| 2004/0039259 A1 | 2/2004 | Krause et al. | |
| 2004/0082849 A1 | 4/2004 | Schweikard et al. | |
| 2004/0097922 A1 | 5/2004 | Mullaney | |
| 2004/0171924 A1 | 9/2004 | Mire et al. | |
| 2004/0230199 A1 | 11/2004 | Jansen et al. | |
| 2004/0243148 A1 | 12/2004 | Wasielewski | |
| 2004/0263535 A1 | 12/2004 | Birkenbach et al. | |
| 2005/0021043 A1 | 1/2005 | Jansen et al. | |
| 2005/0027304 A1 | 2/2005 | Leloup et al. | |
| 2005/0065617 A1 | 3/2005 | Moctezuma de la Barrera et al. | |
| 2005/0075632 A1 * | 4/2005 | Russell | 606/53 |
| 2005/0288679 A1 | 12/2005 | Kienzle | |
| 2006/0015030 A1 | 1/2006 | Poulin et al. | |
| 2006/0064095 A1 | 3/2006 | Senn et al. | |
| 2006/0064106 A1 | 3/2006 | Fernandez | |
| 2006/0084867 A1 | 4/2006 | Tremblay et al. | |
| 2006/0095040 A1 | 5/2006 | Schlienger et al. | |
| 2006/0098851 A1 | 5/2006 | Shoham et al. | |
| 2006/0161059 A1 | 7/2006 | Wilson | |
| 2006/0173293 A1 | 8/2006 | Marquart et al. | |
| 2006/0241416 A1 | 10/2006 | Marquart et al. | |
| 2006/0281334 A1 | 12/2006 | Shin et al. | |
| 2007/0038059 A1 * | 2/2007 | Sheffer et al. | 600/407 |
| 2007/0038223 A1 * | 2/2007 | Marquart et al. | 606/86 |
| 2007/0161929 A1 | 7/2007 | Maier | |
| 2007/0270680 A1 | 11/2007 | Sheffer et al. | |
| 2008/0018643 A1 * | 1/2008 | Feilkas | G06T 7/0051 345/420 |
| 2008/0051910 A1 | 2/2008 | Kammerzell et al. | |
| 2008/0075348 A1 | 3/2008 | Rappaport et al. | |
| 2008/0089566 A1 | 4/2008 | Node-Langlois et al. | |
| 2008/0119725 A1 | 5/2008 | Lloyd | |
| 2008/0243191 A1 | 10/2008 | Tipirneni et al. | |
| 2008/0269596 A1 * | 10/2008 | Revie et al. | 600/424 |
| 2008/0281334 A1 | 11/2008 | Zheng et al. | |
| 2008/0294265 A1 | 11/2008 | Warkentine et al. | |
| 2008/0319448 A1 * | 12/2008 | Lavallee et al. | 606/102 |
| 2009/0209851 A1 | 8/2009 | Blau | |
| 2009/0234217 A1 | 9/2009 | Mire et al. | |
| 2010/0030219 A1 | 2/2010 | Lerner et al. | |
| 2010/0104150 A1 | 4/2010 | Saint Felix et al. | |
| 2010/0168562 A1 * | 7/2010 | Zhao et al. | 600/426 |
| 2011/0019884 A1 | 1/2011 | Blau | |
| 2011/0184477 A1 | 7/2011 | Dell'Oca et al. | |
| 2011/0213379 A1 | 9/2011 | Blau et al. | |
| 2011/0313418 A1 | 12/2011 | Nikonovas | |
| 2013/0060146 A1 | 3/2013 | Yang et al. | |
| 2013/0211244 A1 | 8/2013 | Nathaniel | |
| 2013/0322726 A1 | 12/2013 | Nathaniel | |
| 2017/0128027 A1 | 5/2017 | Nathaniel et al. | |

FOREIGN PATENT DOCUMENTS

| | | |
|---|---|---|
| CN | 101069640 A | 11/2007 |
| DE | 102005062610 A1 | 6/2007 |
| DE | 102005062611 A1 | 6/2007 |
| DE | 102007008521 A1 | 8/2007 |
| DE | 102007008522 A1 | 8/2007 |
| EP | 0738502 A2 | 10/1996 |
| EP | 1440664 A2 | 7/2004 |
| EP | 1491151 A1 | 12/2004 |
| EP | 1523950 A1 | 4/2005 |
| EP | 1859755 A2 | 11/2007 |
| EP | 1994914 A1 | 11/2008 |
| FR | 2895267 A1 | 6/2007 |
| GB | 2421187 A | 6/2006 |
| JP | 2000510730 A | 8/2000 |
| JP | 2005246059 A | 9/2005 |
| JP | 2008514296 A | 5/2008 |
| JP | 2010538753 A | 12/2010 |
| WO | 0209611 A2 | 2/2002 |
| WO | 03105659 A2 | 12/2003 |
| WO | 2003105659 A2 | 12/2003 |
| WO | 2004069040 A2 | 8/2004 |
| WO | 2005087125 A2 | 9/2005 |
| WO | 2007073733 A1 | 7/2007 |
| WO | 2007095917 A2 | 8/2007 |
| WO | 2007095918 A2 | 8/2007 |
| WO | 2007095919 A2 | 8/2007 |
| WO | 2007124099 A2 | 11/2007 |
| WO | 2009087214 A1 | 7/2009 |
| WO | 2011002903 A2 | 1/2011 |
| WO | 2012007054 A1 | 1/2012 |
| WO | 2012084056 A1 | 6/2012 |

OTHER PUBLICATIONS

Communication from EP Application No. 10153136 dated Aug. 17, 2011.

Amir Herman et al.,The International Journal of Medical Robotics and Computer Assisted Surgery, 5; 45-50, Dec. 29, 2008.

(56) References Cited

OTHER PUBLICATIONS

Jagannathan et al., Neurosurg Focus 20, 2, E9, pp. 1-6, 2006.
International Search Report, PCT/EP2009/050210, dated Jun. 16, 2009.
Joskowicz et al., IEEE Transactions on Medical Imaging, IEEE Service Center, Piscataway NJ, US, vol. 24, No. 5, May 1, 2005, pp. 624-635.
PCT International Search Report PCT/EP2010/060314 dated Apr. 6, 2011.
Thomas C. Kienzle III et al., "An Integrated CAD-Robotics System for Total Knee Replacement Surgery", IEEE, 1993.
Ziv Yaniv, Member, IEEE, and Leo Joskowicz, Senior Member, IEEE, Precise Robot-Assisted Guide Positioning for Distal Locking of Intramedullary Nails, IEEE Transactions on Medical Imaging, vol. 24, No. 5, May 2005.
Hofstetter et al., "Computer-Assisted Fluoroscopy-Based Reduction of Femoral Fractures and Antetorsion Correction", Computer Aided Surgery 5:311-325 (2000).
International Search Report for PCT/EP2012/004102 dated Feb. 27, 2013.
Schulz et al., "Evidence Based Development of a Novel Lateral Fibula Plate (VariAx Fibula) Using a Real CT Bone Data Based Optimization Process During Device Development", The Open Orthopaedics Journal, 6:1-7 (2012).
U.S. Office Action for U.S. Appl. No. 13/810,299 dated Jun. 4, 2015.
Guoyan Zheng et al., Precise estimation of postoperative cup alignment from single standard X-ray radiograph with gonadal shielding, Proceedings of the 10th international conference on Medical image computing and computer-assisted intervention, Oct. 29-Nov. 2, 2007, Brisbane, Australia.

\* cited by examiner

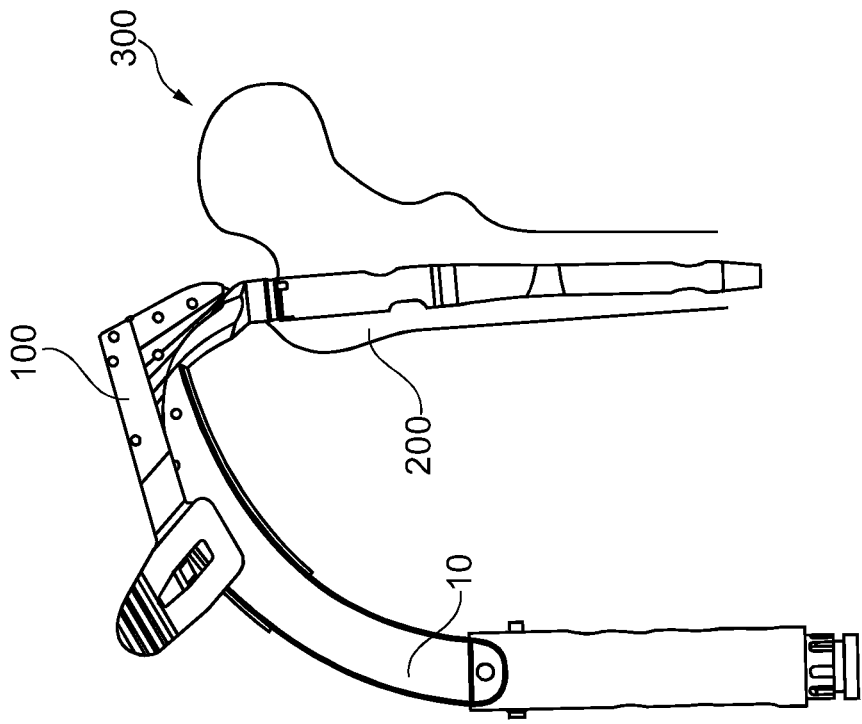
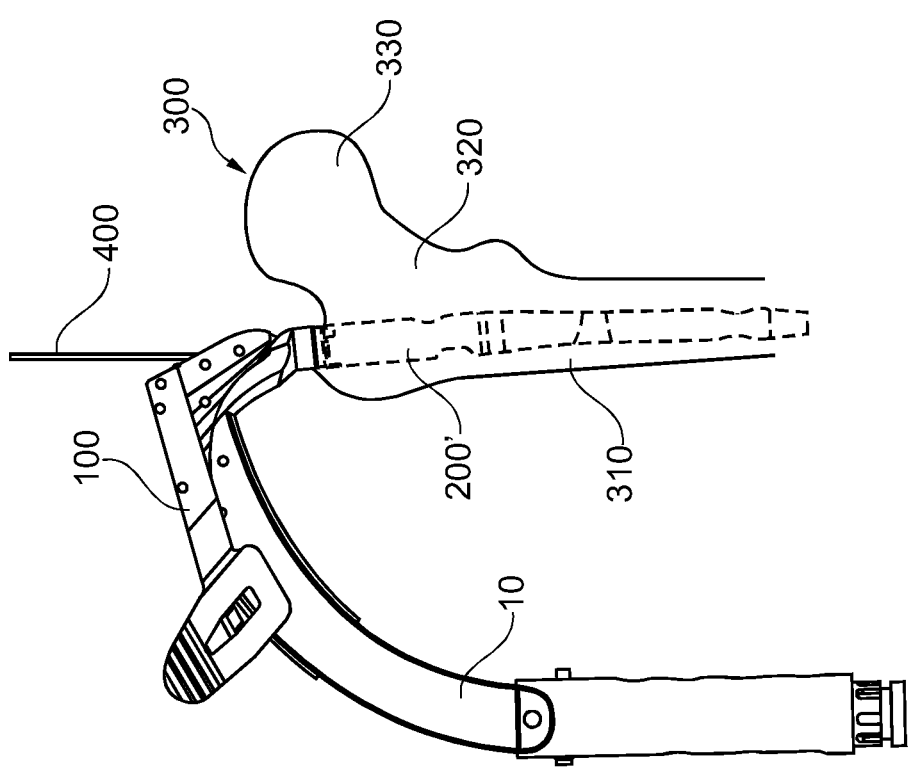

COMPUTER ASSISTED SURGERY SYSTEM

FIELD OF THE INVENTION

The present invention relates to a computer assisted surgery system and a method for operating a computer assisted surgery system, and in particular to a computer assisted surgery system and a method for operating a computer assisted surgery system providing a virtual representation of a medical device to provide an easier application of the medical device, such as an implant or the like.

BACKGROUND OF THE INVENTION

Fractures of the femoral neck, for example, may be treated by intramedullary nailing. In such treatments, a nail for intramedullary nailing typically comprises at least one bore hole for receiving a bone screw. The nail is generally introduced in the longitudinal direction of the femur, wherein the bone screw laterally extends at a certain angle with respect to the neck of the femur when the bone screw is received within the at least one bore hole. A certain problem of the surgeon is to predict the future or implanted position of such a nail or implant or parts thereof. In the past, the operator has acted in a trial and error manner to obtain a more or less optimum position of the implant. However, this may lead to a longer duration of the operation which may lead to higher stress for the patient. Further, for each trial, at least one X-ray image (e.g. a fluoroshot) is generally necessary in order to check the present position of the implant in order to evaluate its position.

"Computer assisted surgery for dynamic hip screw, using Surgix©, a novel intraoperative guiding system" by Amir Herman et al. in *The International Journal of Medical Robotics and Computer Assisted Surgery*, Dec. 29, 2008; Volume 5, pages 45-50, describes a computer assisted surgery system using an image analysis technology in order to measure three-dimensional distances, visualize implant templates, and view a guided trajectory on standard fluoroscopy. A guiding system combines a set of X-ray opaque markers incorporated into transparent hardware as an aiming, positioning, and referring device. This device is attached to a guide wire. Fluoroscopic images are obtained by the surgeon and then are processed by an image processing engine which calculates a three-dimensional orientation relative to a C-arm and a drill trajectory in the image.

Further, a process for the acquisition of information intended for the insertion of a locking screw into an orifice of an endomedullary device is described in EP 1 491 151 B1. This document describes a process for the acquisition of information intended for the insertion of a locking screw into a distal locking hole of an endomedullary device. The described process includes taking two images of different orientations of the distal part of the endomedullary device using a radioscopic unit, acquisition of projection parameters, especially the position of the X-ray source and the projection plane of each image by locating a reference frame fixed on the endomedullary device and optionally another reference frame fixed on the radioscopic unit. The process further includes correcting any distortion of the images, segmenting the distal part of the endomedullary device in each image and calculating the attributes relating to the position of the device and to that of the holes, wherein the attributes comprise at least the contours of the device, its centre of gravity and its principal axis. Further, the process includes constructing the projection cone of the distal part of the device for each image, determining the intersection of the two projection cones, modelling of the endomedullary device on the basis of the intersection, determining a centre of a locking hole with the aid of the modelling and of the centres of gravity of the holes determined on the images, determining the orientation of the locking orifice in an iterative manner, and guiding of a drill tool.

U.S. Patent Publication No. 2009/0209851 filed Jan. 9, 2009, titled "STEREOTACTIC COMPUTER ASSISTED SURGERY METHOD AND SYSTEM" discloses a system and method of computer assisted surgery (CAS) using stereotactic navigation with three-dimensional (3D) visualization, and more specifically to a CAS system that is reactive and does not disrupt operating room workflow procedures, the disclosure of which is incorporated herein by reference in its entirety.

SUMMARY OF THE INVENTION

The present invention provides a computer assisted surgery system and a method for operating a computer assisted surgery system allowing a simple and fast positioning of a medical device to be applied, such as an implant, for example.

According to one embodiment of the invention, there is provided a method for operating a computer assisted surgery system, the method comprising positioning of a reference body in relation to an anatomical structure, the reference body virtually representing a position of a medical device to be applied to the anatomical structure, detecting a position of the reference body in relation to the anatomical structure, superimposing the anatomical structure with a virtual representation of a medical device to be applied based on the detected position of the reference body in relation to the anatomical structure, providing rules for allowable ranges for applying the medical device in relation to the anatomical structure, modifying the position of the reference body, and optimizing the virtual position of the medical device to be applied with respect to the anatomical structure so as to obtain a best fit with respect to the rules for allowable ranges.

Thus, by using a virtual representation of a medical device to be applied, a future position of a real medical device can be predicted without the need of inserting this medical device during the phase of determining the final desired position of the medical device. Thus, the position of the medical device can be virtually optimized before inserting the medical device. This may lead to reducing the stress for the patient with respect to an incision and X-ray impact. Optimizing may include finding of the optimal location, orientation and geometry of the medical device, i.e. the implant. This optimizing may take place supported by a computer device. The reference body may be a particular add-on element as well as a medical tool having a unique geometry to identify the position thereof in imaging.

According to another embodiment of the invention, the position of a medical device includes dimensions, location, and orientation of the medical device.

Thus, the medical device can be virtually represented considering all relevant information with respect to an anatomical structure of the patient. Position may also be the geometry of the medical device, in particular out of a predetermined variety of medical devices.

According to yet another embodiment of the invention, detecting the positioned reference body in relation to an anatomical structure comprises taking two two-dimensional images from different angles and generating a three-dimensional representation based on the two two-dimensional images, and determining a spatial position of the reference body in relation to the anatomical structure based on the three-dimensional representation.

Thus, the anatomical structure as well as the virtual implant or the virtual medical device to be applied can be represented in a three-dimensional manner in order to give an overview over the correct positioning and dimensioning of the medical device to be applied.

According to still yet another embodiment of the invention, modifying may comprise rotating and/or displacing the reference body.

Thus, the reference body representing the position of the medical device can be virtually positioned with respect to the anatomical structure so as to find out the optimized position of the future positioned medical device within the rules provided, wherein the rules provide the allowable ranges for applying the medical device in relation to the anatomical structure.

According to still yet another embodiment of the invention, modifying may comprise selecting the medical device out of a predetermined group of a variety of medical devices.

Thus, for meeting the rules for allowable ranges, also the dimensions of the medical devices can be selected out of a predetermined group in order to find out an optimal implant type to be implanted, for example. The various types may have various geometries, e.g. lengths, inclination angles, and other geometric properties, corresponding to the various anatomical properties.

According to still yet another embodiment of the invention, the method of operating a computer assisted surgery system further comprises imaging the superposition of the anatomical structure and the virtual representation of the medical device to be inserted.

Thus, the surgeon is capable of in-situ controlling and monitoring of the ongoing process of the computer assisted surgery system, which may be of relevance when finally deciding whether the optimization is sufficient and to provide a final check by the surgeon in person.

According to still yet another embodiment of the invention, the position of the medical device to be applied is remote from the reference body. Preferably, the medical device is an implant. Preferably, the reference body is mountable to a medical tool, such as an aiming tool, for example.

Thus, the reference body does not have to be provided in the immediate vicinity of the medical device. Implants may be virtually represented that are not in direct vicinity of the reference body. This is particularly relevant for implants that have a final remote position with respect to an opening location of the incision. Further, also sub-implants can be virtually represented, such as a bone screw of an intramedullary nail, for example, when providing the reference body to an aiming tool.

According to still yet another embodiment of the invention, there is provided a program element, which, when being executed by a processor is adapted to carry out the inventive method for operating a computer assisted surgery system.

According to still yet another embodiment of the invention, there is provided a computer readable medium having stored the inventive program element.

Thus, the method for operating a computer assisted surgery system can be carried out on a computer and a computer program, respectively.

According to still yet another embodiment of the invention, there is provided a computer assisted surgery system comprising a reference body in relation to an anatomical structure, the reference body virtually representing a position of a medical device to be applied to the anatomical structure, a detector device being adapted for detecting a position of the reference body in relation to the anatomical structure, a database including virtual medical device information and a computation device being adapted for superimposing the anatomical structure with a virtual representation of a medical device to be applied, based on an output of the detector device and modifying the position of the reference body and optimizing the virtual position of the medical device to be applied with respect to the anatomical structure so as to obtain the best fit with respect to predetermined rules for allowable ranges for applying the medical device in relation to the anatomical structure.

Such a computer assisted surgery system allows to predict the future position of a medical device to be applied, such as an implant, for example, without the need for a trial and error procedure of a surgeon in order to meet the predetermined rules for allowable ranges for applying the medical device in relation to the anatomical structure, which rules may be provided in form of required distances, for example, to the surface of the bone, particular inclination angles between for example the longitudinal direction of the femur and the orientation of a femoral neck, and the like.

According to an embodiment of the invention, the data base includes a plurality of data sets for the medical device, wherein the data sets represent a variety of medical devices.

Thus, not only the orientation and the location of the medical device can be determined in order to meet the predetermined rules for allowable ranges, but also the dimensions of the medical device as such. This may be of relevance in particular when having a wide variety of anatomies requiring different dimensions with respect to the length, the diameter and particular angles of for example an intramedullary nail and the respective bone screws. According to an embodiment of the invention, the medical device is an implant.

According to still yet another embodiment of the invention, the system further comprises a medical tool being adapted for positioning the implant, wherein the reference body is mountable in a predefined manner to the medical tool.

Thus, the reference body may be used for representing an intramedullary nail, which is still not implanted in order to find the correct position of the intramedullary nail as well as the correct position of the future implanted bone screw before having inserted the intramedullary nail. However, the intramedullary nail may be considered as a reference body, as the intramedullary nail may have a unique form representing also the future position of a bone screw to be inserted. Thus, when having inserted the intramedullary nail being mounted to the medical tool, from the geometry of the intramedullary nail, the future position, i.e. the location, the dimension, and the orientation of the bone screw can be determined. It should be noted that the intramedullary nail can be used as a reference body representing the future position of a bone screw, for example. However, also a separate reference body can be used for representing for example the intramedullary nail, wherein such reference body may be fixed in a predetermined position to the medical tool or the nail in order to represent and predict the future position of the intramedullary nail. When knowing the geometry and orientation of the intramedullary nail, also the future position of a bone screw can be predicted by evaluating the reference body mounted to the medical tool.

It should be noted that the above described embodiments of the invention apply also for the method of operating the computer assisted surgery system, the computer assisted surgery system, the program element as well as the computer readable medium.

It should also be noted that the above feature may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

The present invention will be better understood on reading the following detailed description of non-limiting embodiments thereof, and on examining the accompanying drawings, in which:

FIG. 4a illustrates a virtual representation of the implant.

FIG. 4b illustrates a real position of the implant.

DETAILED DESCRIPTION

Figure 1:
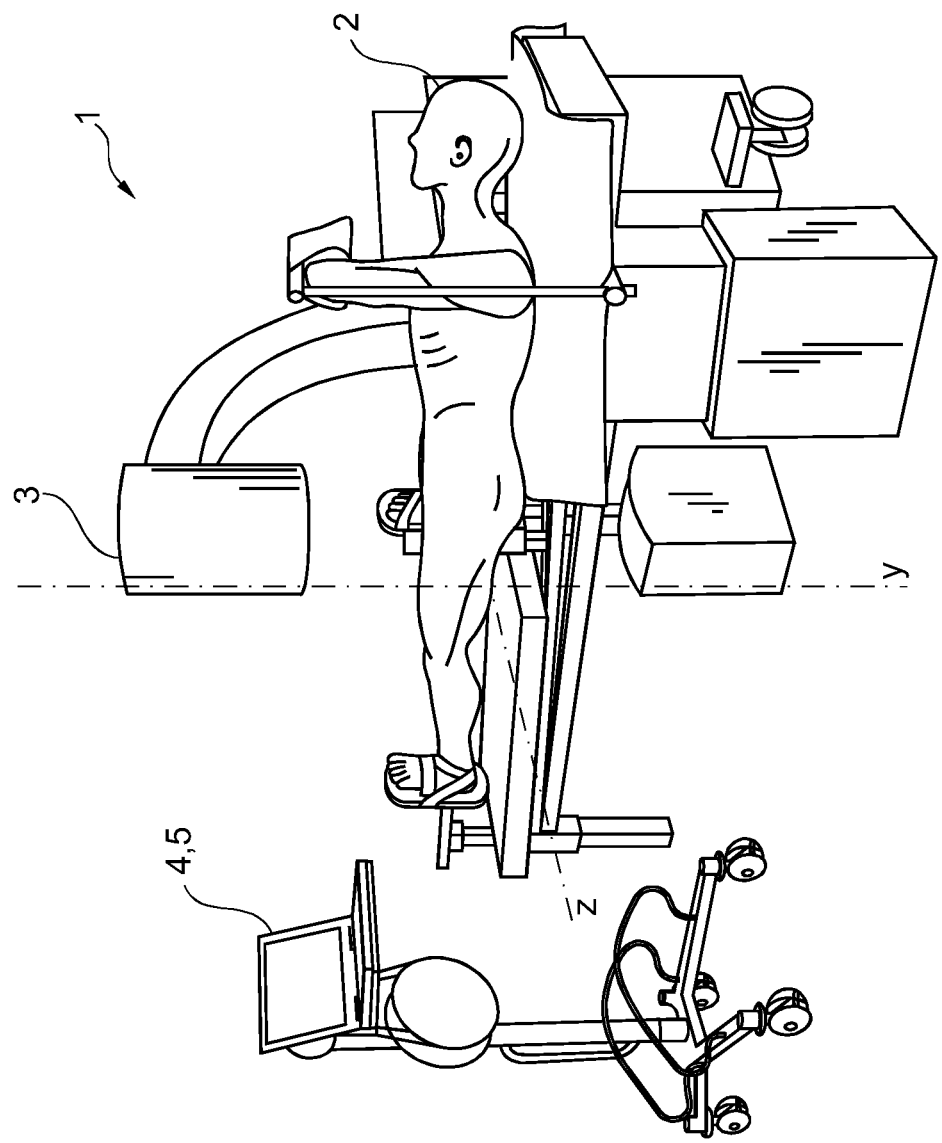
FIG. 1 illustrates a computer assisted surgical system.

FIG. 1 illustrates a computer assisted surgery system 1. A patient 2 can be positioned in or on the computer assisted surgery system so that application of a medical device to be applied, such as an implant, for example, can be assisted. The computer assisted surgery system of FIG. 1 illustrates a configuration for the implantation of the intramedullary nail in the femur of the patient 2. For this purpose, an imaging device 3 is provided in order to deliver images from the location of the anatomical structure for which the application of the implant is intended. The computer assisted surgery system further comprises a display unit 4 as well as a computation unit 5 so that the correct position of the medical device and implant, respectively, can be computed and displayed on the display unit. Thus, the surgeon receives assistance in applying an intramedullary nail and a respective bone screw, for example, so that the total incision time can be reduced and the position of the implant can be improved.

Figure 2:
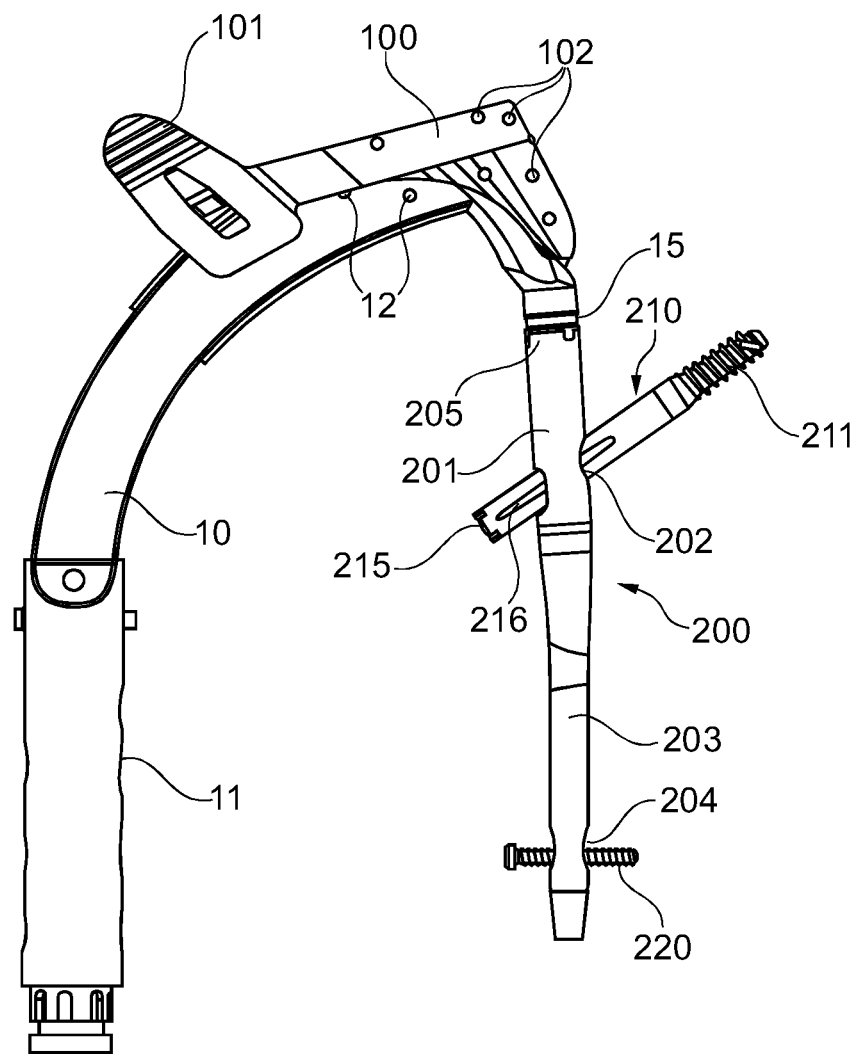
FIG. 2 illustrates a medical tool having fixed thereon a reference body and an implant including an intramedullary nail and a bone screw.

FIG. 2 illustrates a medical application tool 10 in form of an aiming tool. The aiming tool comprises a finger grip 11 and a coupling portion 15 for coupling a medical device 200 to be applied. This medical device in FIG. 2 is an intramedullary nail 200. This intramedullary nail has an upper portion 201 also comprising a coupling portion 205 for coupling the intramedullary nail to the coupling portion 15 of the medical tool 10. In the embodiment shown in FIG. 2, the intramedullary nail 200 comprises an orifice 202 provided in the upper shaft portion 201 of the intramedullary nail. This orifice 202 serves for receiving a bone screw 210. The intramedullary nail further comprises a lower shaft portion 203 comprising a further orifice 204 for receiving a distal fixation screw 220. The bone screw 210 is designed to extend into the neck of femur bone. For this purpose, the bone screw 210 is provided with a gear shaft 211 for a fixation in the bone material. Further, the bone screw is provided with a fixation arrangement 216, so that the bone screw can be fixed within the intramedullary nail 200. This fixation can be carried out by an internal screw along the longitudinal extension of the intramedullary nail in the upper shaft portion 201 so as to fix the position of the bone screw 210 with respect to the intramedullary nail 200. Further, the bone screw 210 can be provided with a receptacle 215 for receiving a respective tool, e.g. a screw driver, for turning the bone screw 210 into the bone, for example the femoral neck.

In FIG. 2, a reference body 100 is fixed in a predetermined manner onto the medical tool 10. The reference body comprises a finger grip 101 for an easier fixation and positioning of the reference body. The reference body further comprises a plurality of fiducial markers 102. These markers are distributed over the reference body in a predefined manner in order to give a unique representation in any two-dimensional projection, so that a single fluoroshot image may be sufficient for determining the unique 3D position of the reference body 100. As the reference body 100 is fixed to the medical tool 10 in a predefined manner, also with respect to the intramedullary nail 200, the known orientation, location, and in general position of the reference body 100 at the same time represents the position of the intramedullary nail 200. In case, the geometry of the intramedullary nail 200 is known, also the position of the bone screw 210 and the distal locking screw 220 is predefined at least for the direction of the longitudinal extension thereof. Thus, the positioning of the medical tool 10 together with the reference body 100 allows to determine the position of the intramedullary nail 200 as well as at least the longitudinal extension direction of the bone screw 210 and the distal locking screw 220, irrespective of the visibility of the intramedullary nail in a fluoroshot image, for example.

In order to determine whether the reference body 100 is correctly positioned with respect to the medical tool 10, also the medical tool 10 can be provided with a plurality of fiducial markers 12, so that the correct position of the reference body with respect to the medical tool 10 can be determined by evaluating a single fluoroshot image.

Figure 3A:
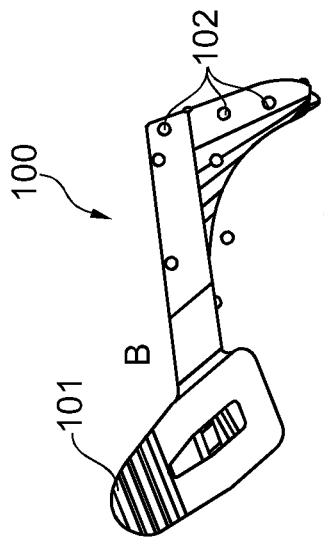
FIG. 3a illustrates the reference body shown in FIG. 3.
Figure 3B:
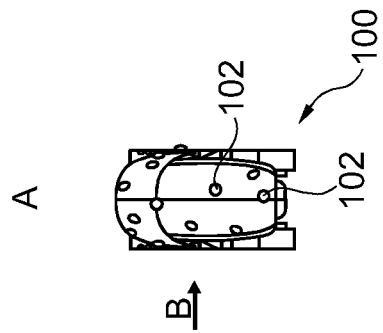
FIG. 3b illustrates an end view of the reference body shown in FIG. 3.
Figure 3:
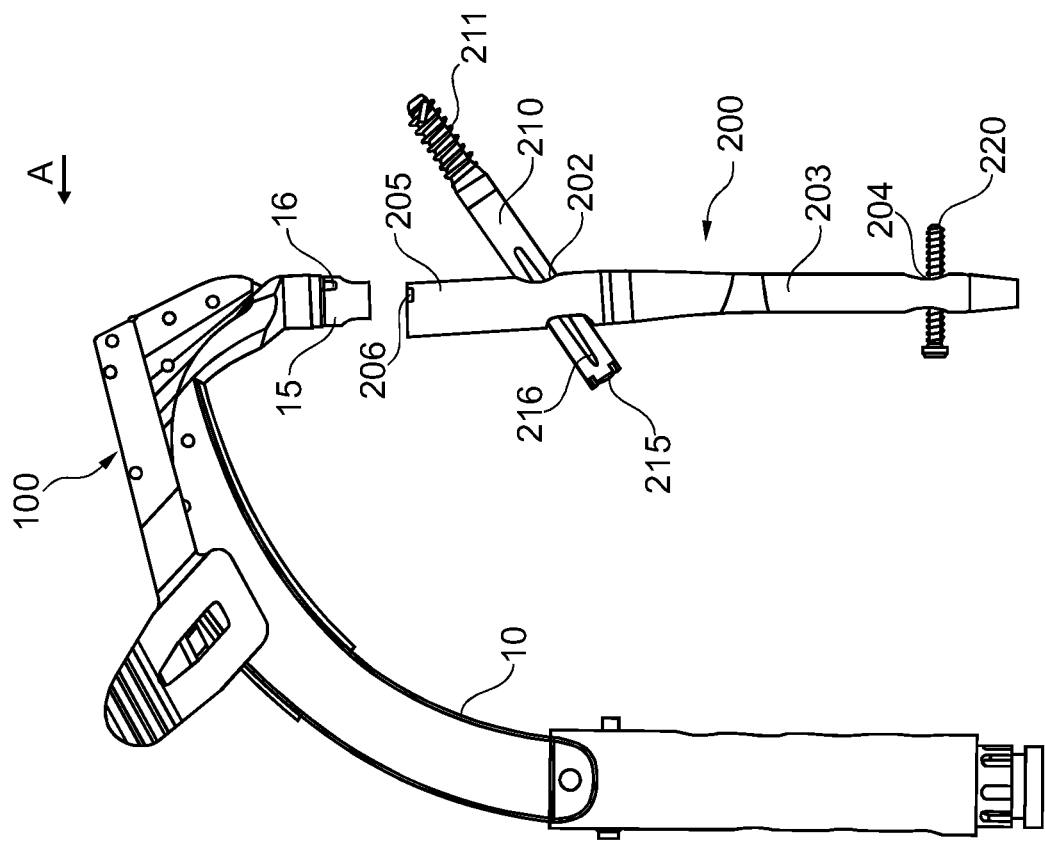
FIG. 3 illustrates the implant being separated from the medical tool shown in FIG. 2.

FIG. 3 illustrates the single elements of the implant portion and the tool portion shown in FIG. 2. FIG. 3 illustrates the intramedullary nail 200 in a released manner with respect to the medical tool 10. The medical tool 10 comprises a coupling portion 15 having a unique matching pattern 16 in form of for example noses for receiving a respective counterpart of the intramedullary nail 206, 205. Thus, a unique matching position of the intramedullary nail 200 with respect to the medical tool 10 can be provided, so that it can be ensured that the reference body 100 can be used for pre-definitely representing the intramedullary nail 200.

FIG. 3a illustrates a front view of the reference body 100. The fiducial markers 202 are irregularly distributed over the reference body 100, however, in a predefined manner, so that a single fluoroshot allows a unique determination of the spatial position of the reference body. FIG. 3b illustrates a side view of the reference body being separated from the medical tool 10.

When knowing the position of an intramedullary nail 200 with respect to the reference body, the variation of the position of the reference body, here mounted onto the medical tool 10, can be used to determine a future position of the intramedullary nail, even if the nail is not mounted to the medical tool 10. This can be seen from FIG. 4a. which illustrates an anatomical structure 300 in form of a femur bone having a femur head 330, a femur neck 320 and femur shaft 310. When positioning the medical tool 10 having mounted thereon the reference body 100, a future position of an intramedullary nail can be determined by visualizing a virtual representation of the intramedullary nail 200'. It should be noted that for the following description, the reference numbers with an apostrophe represent a virtual portion of a medical device to be applied, e.g. an implant, wherein the references without an apostrophe represent the real medical device, also when already applied.

When positioning the medical tool 10 onto the top of the femur bone, the modification of the position of the medical tool together with the reference body 100 allows determining a virtual representation of the later applied medical device. When having found the correct position of the medical device to be implanted, as shown in FIG. 4a, a respective guide wire 400 can be applied to the femur bone so as to fix the point of entry, which belongs to an optimal position of the medical device to be applied. Then, the medical tool 10 can be removed while remaining the guide wire 400 at the femur bone 300. Thus, the entry point is fixed in order to apply a drilling device or an awl for opening the respective entering point of the femur bone. After the drilling, the real intramedullary nail 200 can be coupled to the medical tool 10 in order to insert the intramedullary nail into the femur bone 300, in particular the femur shaft 310, as can be seen from FIG. 4b.

It should be noted that according to the known geometry of the intramedullary nail and the predefined coupling of the intramedullary nail 200 to the medical tool 10 via the predefined coupling arrangement 205, 206, 15, 16, also the direction of the bone screw 210 is defined as well as the direction of the distal locking screw 220.

The reference body may also be mounted to an awl or bore tool, or to a targeting tool for representing an awl. When providing an awl with a reference body, the future position of the nail can be predicted based on the trajectory of the awl. Thus, the future position of the nail can be determined when producing the bore hole, e.g. by an awl or a drilling tool. In other words, it is possible to determine the future nail position in-situ when drilling the hole for the nail.

Figure 5:
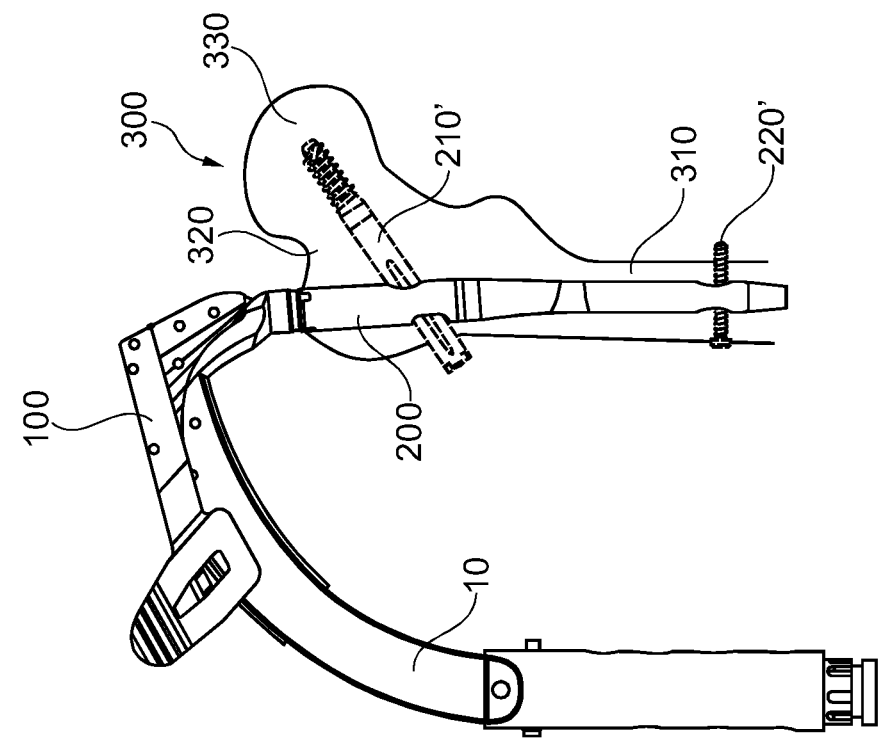
FIG. 5 illustrates a virtual representation of a bone screw and a real position of a nail.

FIG. 5 illustrates starting from FIG. 4b having inserted the real intramedullary nail 200, the virtual representation of the bone screw 210' and the locking screw 220'. Although the exact position of the bone screw as well as the locking screw can be varied, the longitudinal direction and orientation thereof is predefined by the orifices 202, 204 of the intramedullary nail. Thus, when having inserted the intramedullary nail, a virtual representation of the bone screw 210' can be used in order to determine the correct position of the intramedullary nail with respect to a longitudinal translation as well as a rotation with respect to the longitudinal axis of the intramedullary nail. It should be understood, that also the intramedullary nail 200 can be provided with a unique geometry allowing the defined determination of the position of the intramedullary nail, i.e. the location, the dimension, and the orientation thereof. In other words, when using the real intramedullary nail 200 as a reference body, an additional reference body 100 on top of the medical tool may be left out, as the intramedullary nail then may serve as a reference body for the bone screw 210' to be applied as well as a distal locking screw 220' to be applied.

Figure 6:
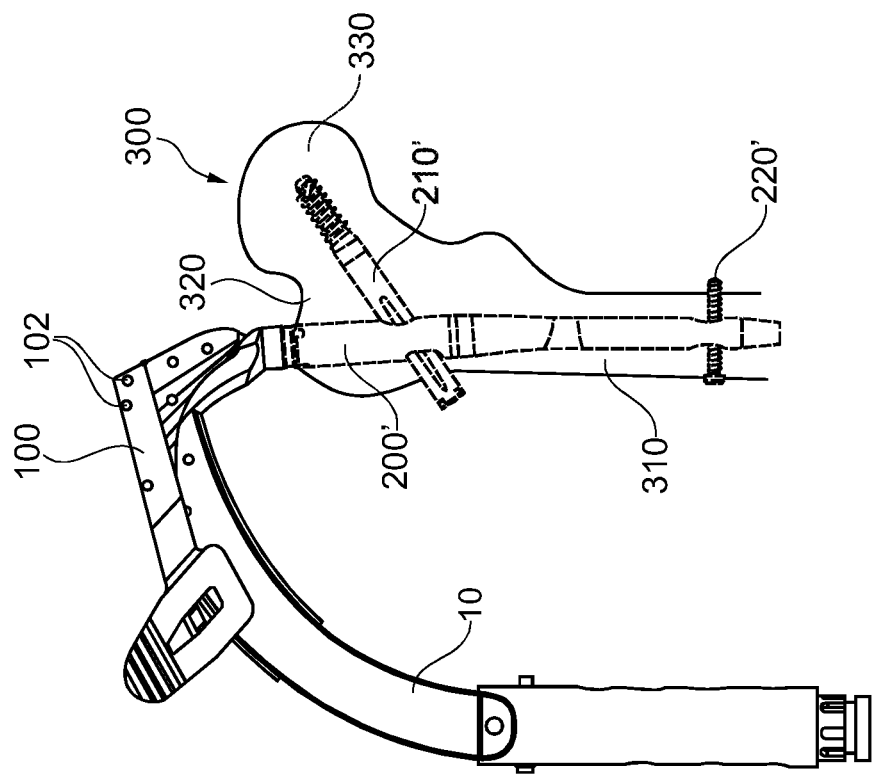
FIG. 6 illustrates a virtual representation of a bone screw and a nail.

FIG. 6 illustrates a virtual representation of the intramedullary nail 200' together with a virtual representation of the bone screw 210' and the distal locking screw 220'. As the position of the bone screw 210' is defined by the orientation thereof with respect to the intramedullary nail 200', the positioning of the medical tool can be used to find the correct position of the intramedullary nail as well as the bone screw. By repositioning of the medical tool 10, the virtual representation of the intramedullary nail 200' together with the bone screw 210' varies, so that the correct position not only of the intramedullary nail but also of the bone screw can be determined. This allows for example to determine the correct axial displacement of the virtual intramedullary nail 200' in order to find the correct position of a virtual bone screw 210' to maintain certain distances between the bone screw and the bone surface of the femoral neck 320. This will be described in greater detail with respect to the following figures.

Figure 7A:
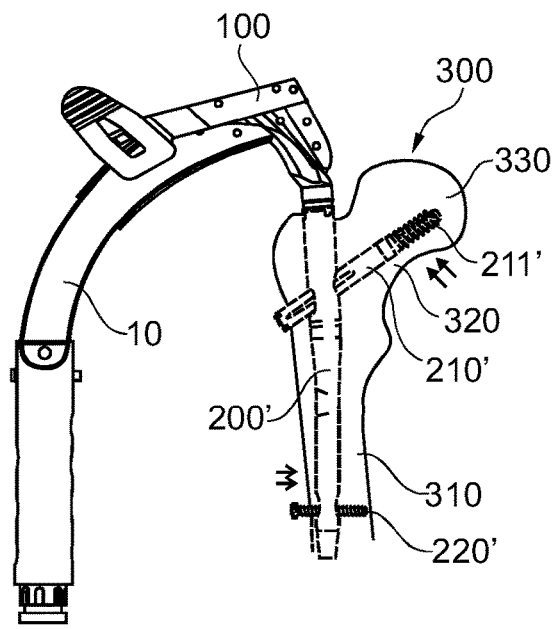
FIG. 7a illustrates a deviation to a first direction of a virtual nail and a virtual screw as shown by the arrows provided.

FIG. 7a illustrates a virtual position of the intramedullary nail 200' together with the virtual representation of the bone screw 210'. However, the virtual representation of the implants, the intramedullary nail as well as the bone screw, illustrates a position, which is not sufficient for a final insertion of the intramedullary nail as well as the bone screw, as the distances of the intramedullary nail to the surface of the femur shaft as well as the distance of the bone screw to the surface of the femur neck are too narrow (see arrows). Thus, the position of the medical tool 10 has to be modified in order to find a better positioning.

Figure 7B:
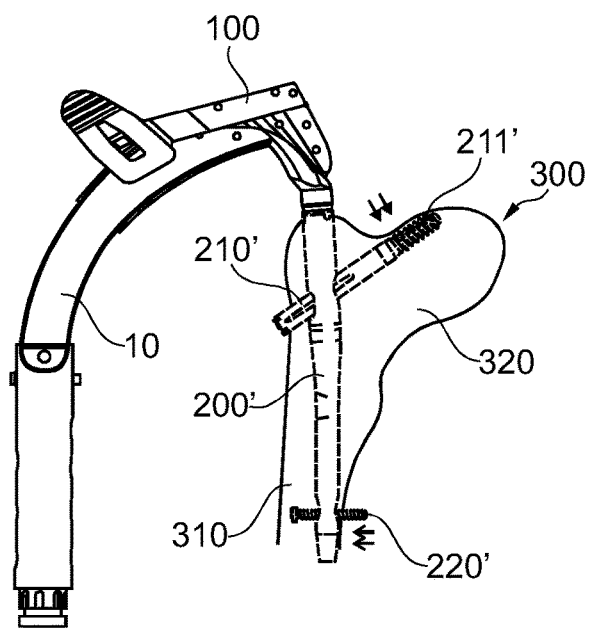
FIG. 7b illustrates a deviation to a second direction of a virtual nail and a virtual screw as shown by the arrows provided.

FIG. 7b illustrates a repositioning, however, this positioning is also not suitable for a final insertion of the implant, as the virtual representation of the intramedullary nail 200' as well as the virtual representation of the bone screw 210' is again too narrow to the surface of the femur shaft 310 and the femur neck 320, respectively. After a further repositioning, according to FIG. 7c, a correct position of the virtual intramedullary nail 200' and a virtual representation of the bone screw 210' is achieved, so that the correct position can be fixed, for example by applying a guide wire 400. After having fixed the correct point of entry, the entire real implant, i.e. the intramedullary nail 200 and the bone screw 210 can be applied to the femur bone 300 in the previously determined position. It should be noted that according to the unique representation of the reference body 100, uniquely representing the intramedullary nail as well as the direction of the bone screw, no further fluoroscopic shots are required between FIGS. 7*a* and 7*c*. Another fluoroscopic shot may be taken if controlling the final implant position is desired to confirm a successful implantation thereof, as illustrated in FIG. 7*d*.

Figure 7C:
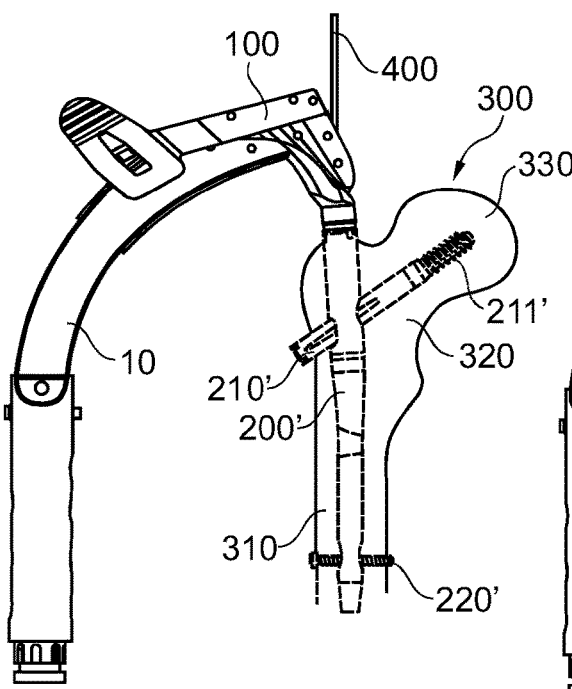
FIG. 7c illustrates a correct position of a virtual nail and a virtual screw.
Figure 7D:
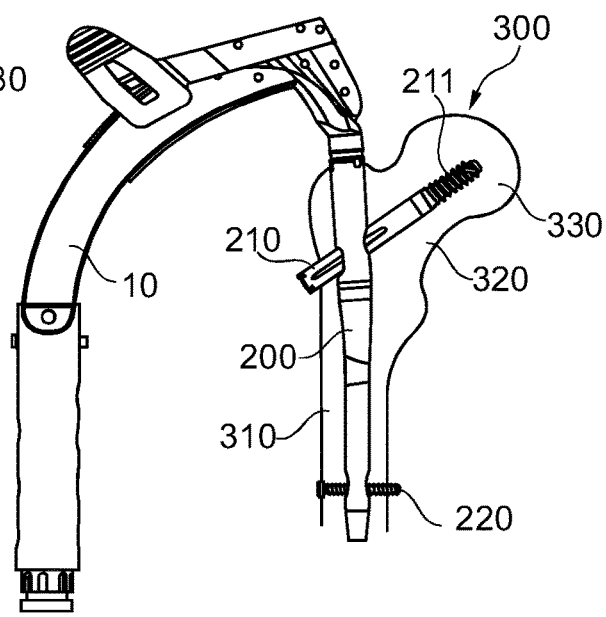
FIG. 7d illustrates a final position of a real nail and a real screw.

As shown in FIG. 7*c*, in the case where the correct point of entry is determined, the intramedullary nail 200 can be coupled to the medical tool 10 and then can be inserted into the femur shaft 310. Either the intramedullary nail 200 or the reference body 100 or both, the reference body 100 and the intramedullary nail 200, can be used as a reference body 100 in order to virtually represent the bone screw 210' and a virtual representation of the distal locking screw 220'. By repositioning the medical tool 10 together with the intramedullary nail 200, the correct future position of the bone screw 210' can be determined.

Figures 8A, 8B:
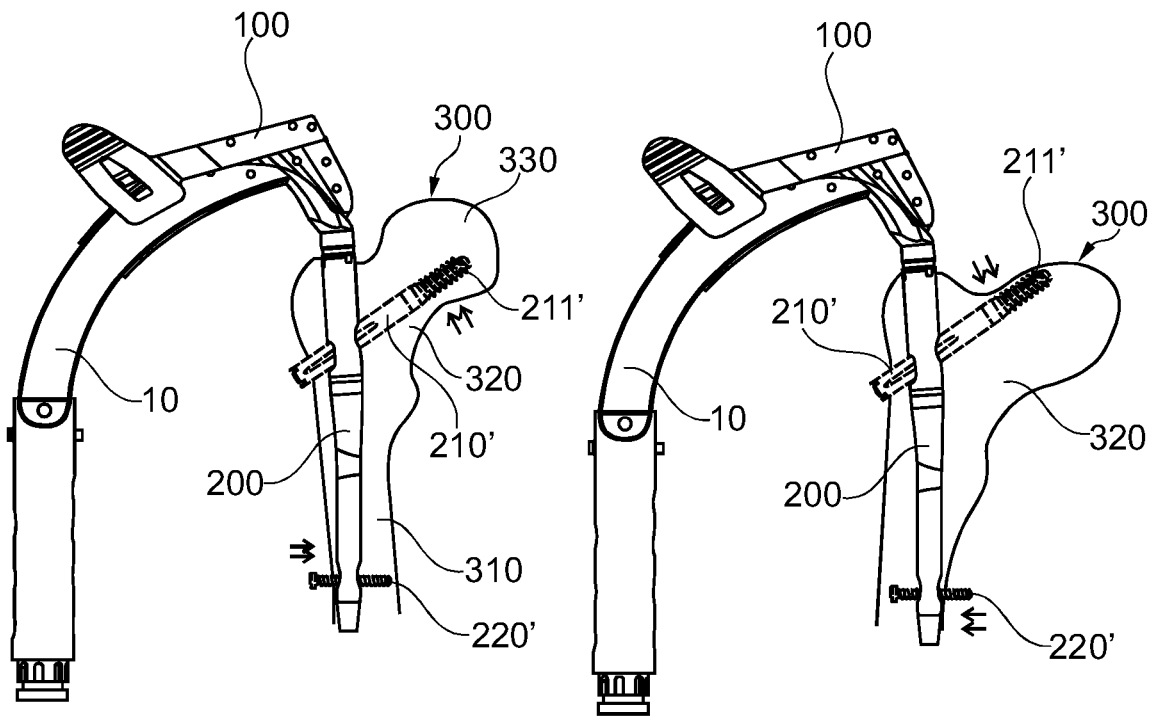
FIG. 8a illustrates a deviation to a first direction of a real nail and a virtual screw as shown by the arrows provided.
FIG. 8b illustrates a deviation to a second direction of a real nail and a virtual screw as shown by the arrows provided.
Figures 8C, 8D:
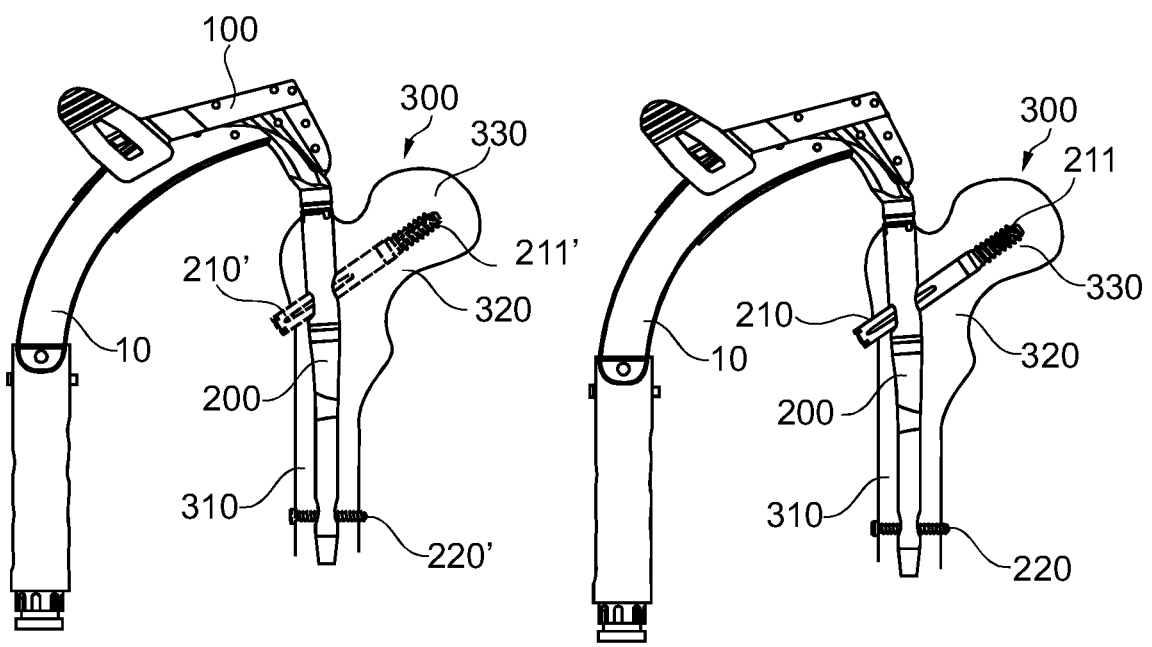
FIG. 8c illustrates a correct position of a real nail and a virtual screw.
FIG. 8d illustrates a final position of a real nail and a real screw.

FIGS. 8*a* to 8*d* illustrate the placement of a virtual representation of a bone screw 210' when having positioned a real nail 200. FIG. 8*a* illustrates an insufficient position with respect to the low distance between the virtual bone screw 210' to the surface of the femur neck 320 (arrows), whereas FIG. 8*b* illustrates a counter-positioned insufficient positioning with respect to the other side of the femur neck (arrows). FIG. 8*c* illustrates a better position of the intramedullary nail 200 with respect to the virtually representation of the bone screw 210', so that the real bone screw 210 can be inserted as shown in FIG. 8*d*. It should be noted that the reference body 100 can also be used to represent for example a boring tool in order to provide a bore hole into the shaft of the femur neck 310, so that during the drilling process, the correct position of the driller can be monitored without the need for single fluoroshot images during the drilling procedure. The reference body may also represent the nail 200' when drilling a bore hole so that the correct positioning of the nail can be monitored when drilling the hole for receiving the later nail. This monitoring of the drilling procedure is similar to the illustration of FIG. 8*a* to 8*c*, wherein the intramedullary nail 200 then is replaced by a driller, whereas the virtual representation of the bone screw 210' may be maintained in order to ensure the correct position of the bone screw 210.

It should be noted that the computer assisted surgery system may also assist in finding a better position or orientation of the reference body 100, 200. This can happen by giving detailed instructions to the surgeon in which the aiming tool direction should be moved to find the correct position. It is also possible to give a haptic feedback to the handgrip of the aiming tool, for example, so that the surgeon can directly recognize in which direction he should move the aiming tool. For this purpose respective actors can be placed to the handle or grip.

Figure 9A:
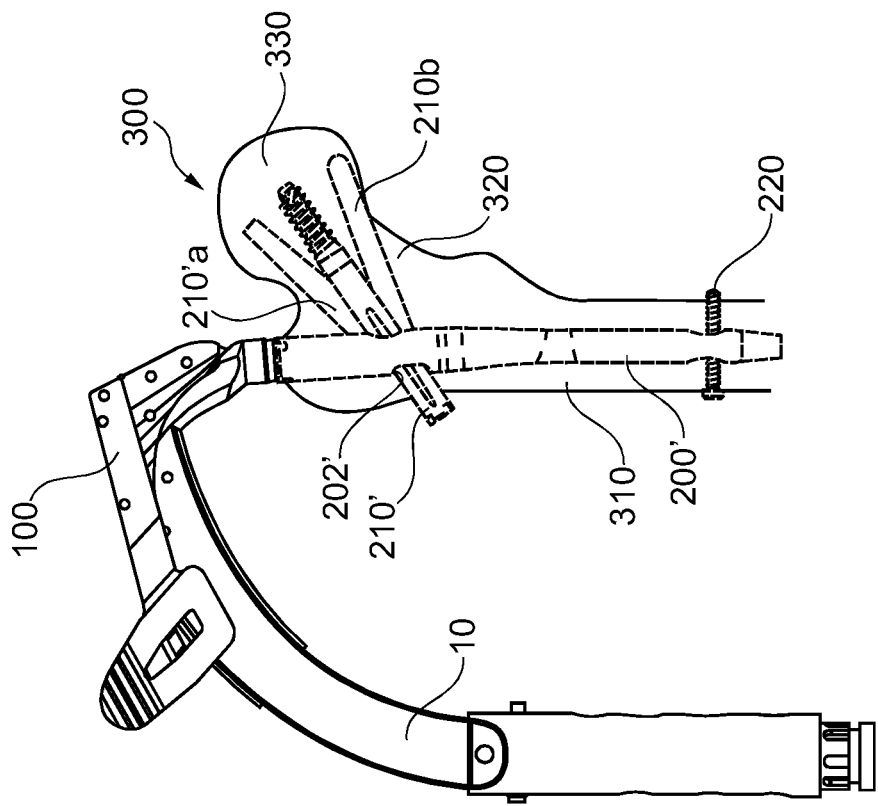
FIG. 9a illustrates a virtual representation of a variety of different geometries, i.e. inclination angles of a screw with respect to a nail.

FIG. 9*a* illustrates the visualization of the virtual representation of an intramedullary nail having a varying geometry of the orifice 202. By selecting a respective virtual intramedullary nail 200', the inclination of the bone screw 210' can be varied to a steeper position 210*a*' or a less inclined position 210*b*'. Thus, by virtually representing a variation of possible intramedullary nails allowing different inclination angles of the bone screw 210', the correct type of intramedullary nail can be selected in order to achieve the correct positioning of the later implanted bone screw 210. This selection can be carried out by the computer assisted surgical system when searching for an optimum geometry in the database and proposing the respective type of implant.

Figure 9B:
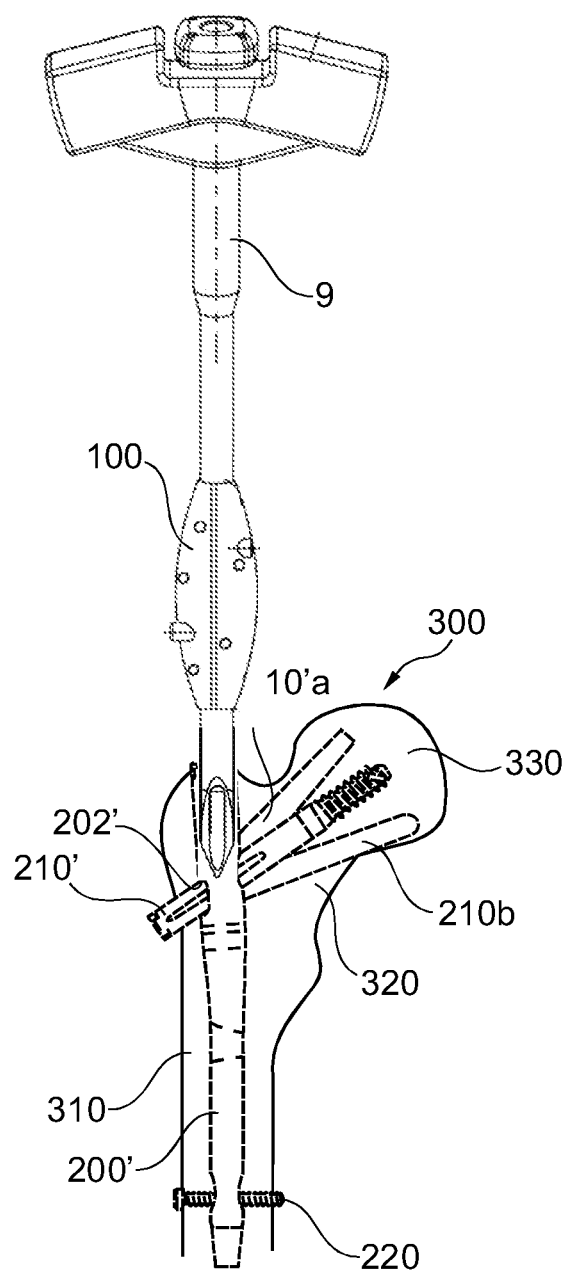
FIG. 9b illustrates a virtual representation of a variety of different geometries, i.e. inclination angles of a screw with respect to an awl.

In practice stereotaxis with intra-operative X-ray imaging is used, wherein an awl 9 provided with a reference body 100 may be used to drill a bore hole for the nail, as illustrated in FIG. 9*b*. The system may detect the reference body 100 of the awl 9 and thus knows the axis of implant 200', e.g. the axis of the gamma nail/intramedullary nail in 3D space. When having entered the bone for a certain distance, the trajectory of the awl 9 is substantially determined. However, slight corrections may be carried out depending on the depth of the awl. By producing two two-dimensional images, e.g. one in the AP-direction and one in the ML-direction, the anatomic structure can be visualized together with the already entered awl. In ML view, the system segments the femoral head and thus knows the centre of the femoral head, and is thus able to calculate correct rotation of implant in ML view. In AP view, the system overlays the implant with correct axis rotation as calculated in ML, performs automatic segmentation of femoral head, thus calculates the centre of the femoral head (or the Apex). The virtual representation of the nail allows to rotate and/or to translate the reference body so as to find the optimized position for the nail. The system then may virtually move the implant e.g. the nail along the trajectory corresponding to the nail axis until trajectory of bone screw, e.g. for 125° inclination angle between nail 200' and bone screw 210' as default, runs through head centre (or Apex) and displays, in addition to the default type, all other available types of implant. This may be carried out by a software tool. The optimal nail position and optimal nail type may be determined automatically by the computation device based on the available data sets of the database so that the surgeon may receive a proposal for the nail position and the nail type, as well as the corresponding bone screw and/or the distal locking screw. Optionally the user may interact with the system to adapt entry depth of nail. Optionally the system may present a 3D reconstruction of whole scenery. The already introduced awl provides a stable position in the bone so that the future position of the intramedullary nail can be provided. Further, the rigid position of the awl allows maintaining the position in the operation process. In other words, the entire work flow of the operation will not be disturbed when using the computer assisted surgery system. It should be noted that the illustrations of FIGS. 2 to 10 are illustrations in the AP-direction, and that corresponding illustrations may also be obtained in ML-direction to be fed with the computational unit 5.

In practice, an awl provided with a reference body may be used to drill a bore hole for the nail. When having entered the bone for a certain distance, the trajectory of the awl is substantially determined. However, slight corrections may be carried out depending on the depth of the awl. By producing two two-dimensional images, e.g. one in the AP-direction and one in the ML-direction, the anatomic structure can be visualized together with the already entered awl. The virtual representation of the nail allows to rotate and/or to translate the reference body so as to find the optimized position for the nail. The optimal nail position and optimal nail type may be determined automatically by the computation device based on the available data sets of the data-base so that the surgeon may receive a proposal for the nail position and the nail type, as well as the corresponding bone screw and/or the distal locking screw.

Figure 10:
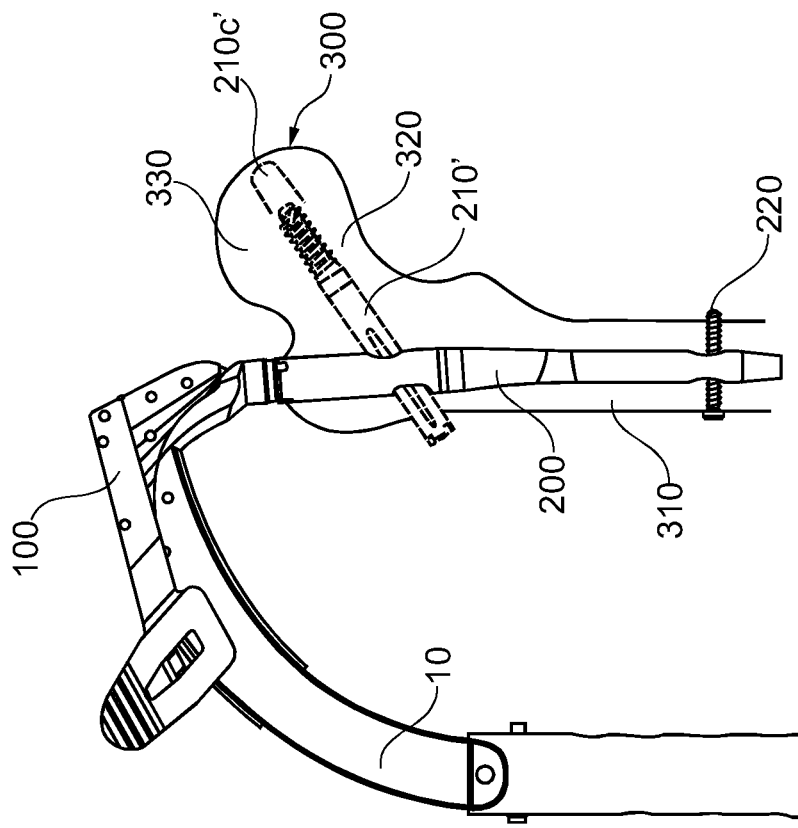
FIG. 10 illustrates a virtual representation of a variety of different geometries, i.e. lengths of a screw with respect to a real nail.

FIG. 10 illustrates in a similar way the selection of the correct bone screw 210 out of a variety of bone screws, so that the required distances of the bone screw to the surface of the femur head 330 can be maintained. FIG. 10 illustrates two possible lengths of a bone screw 210' and 210c', wherein the system based on the rules for allowable ranges should select the position 210', as the longer bone screw 210c' does not maintain the required distance to the surface of the bone head 330.

Figure 11:
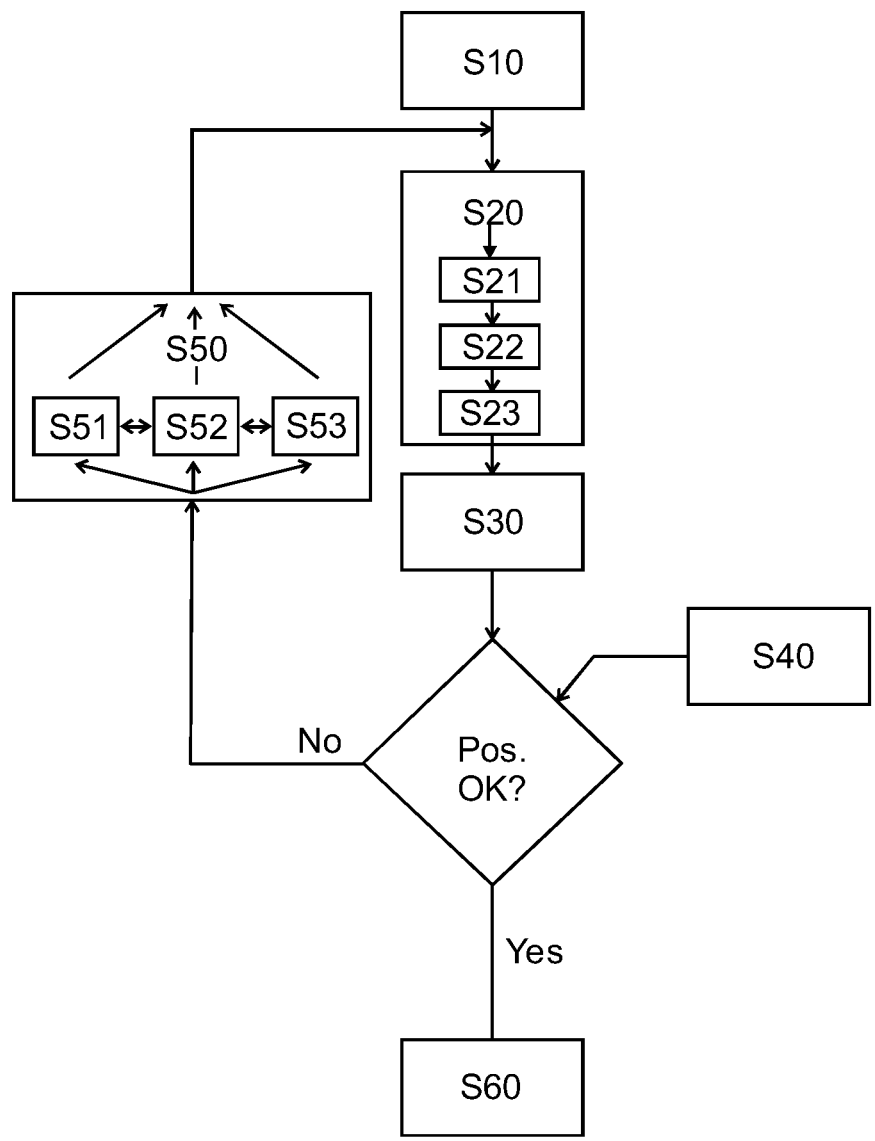
FIG. 11 illustrates a schematic flow diagram of the method for operating a computer assisted surgical system.

FIG. 11 illustrates the method for operating a computer assisted surgery system. The method comprises the positioning S10 of a reference body 100, 200 in relation to an anatomical structure 300, the reference body virtually representing a position of a medical device 200, 210, 220 to be applied to the anatomical structure, detecting S20 a position of the reference body in relation to the anatomical structure, superimposing S30 the anatomical structure with a virtual representation 200'; 210', 220' of a medical device to be applied, based on the detected position of the reference body in relation to the anatomical structure, providing rules S40 for allowable ranges for applying the medical device in relation to the anatomical structure, modifying S50 the position of the reference body and optimizing S60 the virtual position of the medical device to be applied with respect to the anatomical structure so as to obtain a best fit with respect to the rules for allowable ranges. Detecting S20 the positioned reference body 100; 200 in relation to an anatomical structure may further comprise taking two 2-dimensional images from different angles S21, generating a 3-dimensional representation based on the two 2-dimensional image S22, and determining a spatial position of the reference body in relation to the anatomical structure based on the 3-dimensional representation S23. Modifying S50 may comprise rotating S51 and/or displacing S52 of the reference body 100; 200, as well as selecting the medical device 200; 210, 220 out of a predetermined group of a variety of medical devices S53.

In another embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an embodiment of the method as described above.

According to a further embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

It has to be noted that embodiments of the invention are described with reference to different subject matters. In particular, some embodiments are described with reference to apparatus type claims whereas other embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

The invention claimed is:

1. A method of operating a computer assisted surgery system, the method comprising:
 positioning an aiming tool adjacent a femur;
 detecting a position of a reference body having a multiplicity of x-ray opaque fiducial markers distributed in a 3-dimensional arrangement in the reference body based on image data obtained from a first fluoroscopic 2-dimensional image of the femur taken at a first angle, the reference body being coupled to the aiming tool in a pre-defined manner;
 determining the position of the reference body in relation to the femur using the first fluoroscopic 2-dimensional image, the reference body virtually representing a position of an intramedullary nail and a bone screw extending through an opening in the intramedullary nail to be implanted in the femur, the virtual representation of the position of the intramedullary nail being based on a pre-defined relationship between the aiming tool and the intramedullary nail;
 obtaining a second fluoroscopic 2-dimensional image of the femur taken at a second angle different from the first angle;

constructing a 3-dimensional representation of the femur from the first and second fluoroscopic images;

superimposing the 3-dimensional representation of the femur with a virtual representation of the intramedullary nail and the bone screw to be implanted, based on the detected position of the reference body x-ray opaque fiducial markers in relation to the 3-dimensional representation of the femur during the surgical procedure;

providing rules for allowable ranges for applying the intramedullary nail and the bone screw in relation to the 3-dimensional representation of the femur, the allowable ranges including a minimum distance between the bone screw and a surface of a head of the femur;

determining during the surgical procedure from the first and second fluoroscopic images an optimal position of the virtual representation of the intramedullary nail and the bone screw to be implanted with respect to the 3-dimensional reconstruction of the femur so as to obtain a best fit with respect to the rules for allowable ranges based only on image data obtained from the first and second fluoroscopic 2-dimensional images; and displaying the optimal position of the intramedullary nail and the bone screw virtually, the intramedullary nail having an opening with a specific inclination relative to the longitudinal axis of the intramedullary nail for receiving the bone screw, the virtually displayed optimal position of the bone screw having a longitudinal direction and an orientation that are predefined by the opening of the intramedullary nail, and the intramedullary nail and the bone screw being selected out of a predetermined group of a variety of intramedullary nails and bone screws, wherein the intramedullary nail is configured to be coupled to the aiming tool in the pre-defined relationship, and the virtual representation of the position of the intramedullary nail is determined when the intramedullary nail is coupled to neither the aiming tool nor the reference body.

2. The method of claim 1, wherein the position of an intramedullary nail and the bone screw includes dimensions, location and orientation of the intramedullary nail and the bone screw.

3. The method of claim 1, further comprising:
taking a second 2-dimensional image of the reference body and the femur at a second angle different from the first angle;
viewing a 3-dimensional representation generated from the first and second 2-dimensional images.

4. The method of claim 3, wherein the first and second 2-dimensional images include the femur receiving the intramedullary nail and the bone screw.

5. The method of claim 4, wherein the position of the intramedullary nail and the bone screw in relation to the femur is based on the 3-dimensional representation.

6. The method of claim 1, wherein modifying the position of the reference body comprises a surgeon rotating and/or displacing the reference body during the surgical procedure.

7. The method of claim 1, further comprising imaging the superposition of the femur and the virtual representation of the intramedullary nail and the bone screw to be implanted.

8. The method of claim 1, wherein the position of the intramedullary nail and the bone screw to be implanted is remote from the reference body.

9. The method of claim 1, wherein the aiming tool includes a coupling portion having a matching pattern for receiving a respective counterpart of the intramedullary nail in the pre-defined relationship.

10. The method of claim 1, wherein the aiming tool includes a plurality of fiducial markers for use in confirming that the reference body is coupled to the aiming tool in the pre-defined manner.

11. A computer assisted surgery system comprising:
an aiming tool;
a reference body having a multiplicity of x-ray opaque fiducial markers distributed in a 3-dimensional arrangement in the reference body positionable in relation to a 3-dimensional representation of a femur, the reference body virtually representing a position of an intramedullary nail with a bone screw extending through an opening therein to be implanted in the femur, the reference body being coupled to the aiming tool in a pre-defined manner;
a fluoroscopic detector device being adapted for detecting a position of the x-ray opaque fiducial markers reference body in relation to the 3-dimensional representation of the femur;
a database including information of virtual intramedullary nails and bone screws; and
a processor being adapted for superimposing the 3-dimensional representation of the femur with a virtual representation of an intramedullary nail and the bone screw to be implanted based on a single x-ray image output of the fluoroscopic detector device of the 3-dimensional arrangement of the fiducial markers, and modifying the position of the reference body during a surgical procedure, wherein the modifying comprises selecting the intramedullary nail and the bone screw out of a predetermined group of a variety of intramedullary nails and bone screws, and optimizing the position of a virtual representation of the intramedullary nail and the bone screw to be implanted with respect to the 3-dimensional representation of the femur so as to obtain a best fit with respect to predetermined rules for allowable ranges for applying the intramedullary nail and the bone screw in relation to the femur, the allowable ranges including a minimum distance between the bone screw and a surface of a head of the femur; and
a display for visually indicating the optimized position of an actual intramedullary nail and the bone screw based on the optimized position of the virtual intramedullary nail and the bone screw, the intramedullary nail opening having a specific inclination relative to a longitudinal axis of the intramedullary nail for receiving the bone screw, the virtually indicated optimized position of the bone screw having a longitudinal direction and an orientation that are predefined by the opening of the intramedullary nail,
wherein the virtual representation of the position of the intramedullary nail is based on a pre-defined relationship in which the aiming tool is configured to couple to the intramedullary nail, and the virtual representation of the position of the intramedullary nail is configured to be determined when the intramedullary nail is coupled to neither the aiming tool nor the reference body.

12. The system of claim 11, wherein the database includes a plurality of data sets for the intramedullary nail and the bone screw, wherein the data sets represent a variety of different intramedullary nails and bone screws.

13. The system of claim 11, wherein the aiming tool includes a coupling portion having a matching pattern for receiving a respective counterpart of the intramedullary nail in the pre-defined relationship.

14. The system of claim 11, wherein the aiming tool includes a plurality of fiducial markers for use in confirming that the reference body is coupled to the aiming tool in the pre-defined manner.

15. A method for implanting an intramedullary nail having a bone screw extending through an opening therein, the opening inclined with respect to a longitudinal axis of the nail, using a computer assisted surgery system during a surgical procedure, the method comprising:

positioning an aiming tool adjacent a femur;

positioning a reference body in relation to the femur, the reference body having a plurality of x-ray opaque fiducial markers distributed in a 3-dimensional pattern over the reference body in a manner giving a unique spatial representation in any 2-dimensional image for determining a 3-dimensional position of the reference body, the reference body capable of virtually representing a position of a intramedullary nail with the bone screw therein to be implanted in the femur, the reference body being coupled to the aiming tool in a pre-defined manner, wherein the reference body is capable of virtually representing the position of the intramedullary nail based on a pre-defined relationship between the aiming tool and the intramedullary nail, and the virtual representation of the position of the intramedullary nail is configured to be determined when the intramedullary nail is coupled to neither the aiming tool nor the reference body;

taking a first and second fluoroscopic 2-dimensional image of the reference body and x-ray opaque markers and the femur at a first angle and a second angle;

viewing the fluoroscopic image data obtained from the first and second 2-dimensional image on a visual display;

displaying the optimal position of the intramedullary nail and the bone screw virtually, the intramedullary nail having an opening with a specific inclination relative to the longitudinal axis of the intramedullary nail for receiving the bone screw and the intramedullary nail and the bone screw being selected out of a predetermined group of a variety of intramedullary nails and bone screws, the virtually displayed optimal position of the bone screw having a longitudinal direction and an orientation that are predefined by the opening of the intramedullary nail;

viewing the femur with a virtual representation of the selected intramedullary nail and the bone screw to be implanted superimposed on the displayed first and second 2-dimensional image data during the surgical procedure;

determining, using fluoroscopic image data of the reference body and x-ray opaque markers from a single image, an optimal 3-dimensional position of the virtual representation of the selected intramedullary nail and the bone screw to be implanted with respect to the femur so as to obtain an optimal position for implanting the selected intramedullary nail and the bone screw into the femur, the determined optimal 3-dimensional position being based on a minimum distance between the bone screw and a surface of a head of the femur;

coupling the selected intramedullary nail to the reference body and inserting the selected nail into the femur;

modifying the position of the reference body with the selected nail coupled thereto during the surgical procedure based on the optimal position of the virtual representation of the selected intramedullary nail and the bone screw; and implanting the selected intramedullary nail and the bone screw in the optimal position in the femur based on the optimal position of the virtual representation of the selected intramedullary nail and the bone screw.

* * * * *